United States Patent
Kilian et al.

(10) Patent No.: US 7,030,381 B2
(45) Date of Patent: Apr. 18, 2006

(54) METHOD FOR DETECTING A GAS USING AN INFRARED GAS ANALYSER AND GAS ANALYSER SUITABLE FOR CARRYING OUT SAID METHOD

(75) Inventors: Ralf Kilian, Köln (DE); Randolf Rolff, Kerpen-Horrem (DE); Gerhard Küster, Köln (DE); Ralf Hirche, Köln (DE)

(73) Assignee: Inficon GmbH, (DE)

( * ) Notice: Subject to any disclaimer, the term of this patent is extended or adjusted under 35 U.S.C. 154(b) by 216 days.

(21) Appl. No.: 10/450,237

(22) PCT Filed: Nov. 17, 2001

(86) PCT No.: PCT/EP01/13298

§ 371 (c)(1),
(2), (4) Date: Jun. 10, 2003

(87) PCT Pub. No.: WO02/48686

PCT Pub. Date: Jun. 20, 2002

(65) Prior Publication Data

US 2004/0051043 A1 Mar. 18, 2004

(30) Foreign Application Priority Data

Dec. 13, 2000 (DE) ................ 100 62 126

(51) Int. Cl.
*G01N 21/35* (2006.01)

(52) U.S. Cl. .................................... 250/343

(58) Field of Classification Search ............. 250/343
See application file for complete search history.

(56) References Cited

U.S. PATENT DOCUMENTS

| 3,958,122 | A | * | 5/1976 | Jowett et al. ............ 250/346 |
| 4,253,770 | A | * | 3/1981 | Horiba ................... 250/343 |
| 4,393,304 | A |   | 7/1983 | Ishida et al. |
| 5,063,275 | A | * | 11/1991 | Rosenfeld et al. ....... 250/343 |
| 5,563,335 | A |   | 10/1996 | Howard |
| 6,274,870 | B1 | * | 8/2001 | Kubo et al. ............. 250/343 |
| 6,289,718 | B1 | * | 9/2001 | Stock ..................... 73/23.2 |

FOREIGN PATENT DOCUMENTS

| DE | 25 57 405 A1 | 6/1976 |
| DE | 40 12 454 C1 | 8/1991 |
| DE | 43 21 717 A1 | 1/1995 |
| DE | 195 48 348 C1 | 2/1997 |
| DE | 196 46 825 A1 | 5/1998 |
| DE | 199 11 260 A1 | 9/2000 |
| EP | 0 405 841 A2 | 1/1991 |
| WO | WO 200055603 A1 * | 9/2000 |

* cited by examiner

Primary Examiner—Constantine Hannaher
(74) Attorney, Agent, or Firm—Wall Marjama & Bilinski LLP

(57) ABSTRACT

A method for detecting a test gas present at a measuring location, using an infrared gas analyzer having a cuvette, an infrared light source, an infrared detector, and two gas lines. A first gas line is adapted to take up a measuring gas at a measuring location that may contain a test gas to the cuvette. The second gas line is adapted to take up gas from the surroundings of the measuring location (i.e., reference gas), that may contain a test gas background that is to be taken into consideration when detecting the test gas taken up at the measuring location. To improve the sensitivity of the analyzer, only one cuvette and the measuring gas is taken up at the measuring location and the reference gas is fed to the cuvette such that each gas is alternately present therein.

40 Claims, 3 Drawing Sheets

Figure 1:
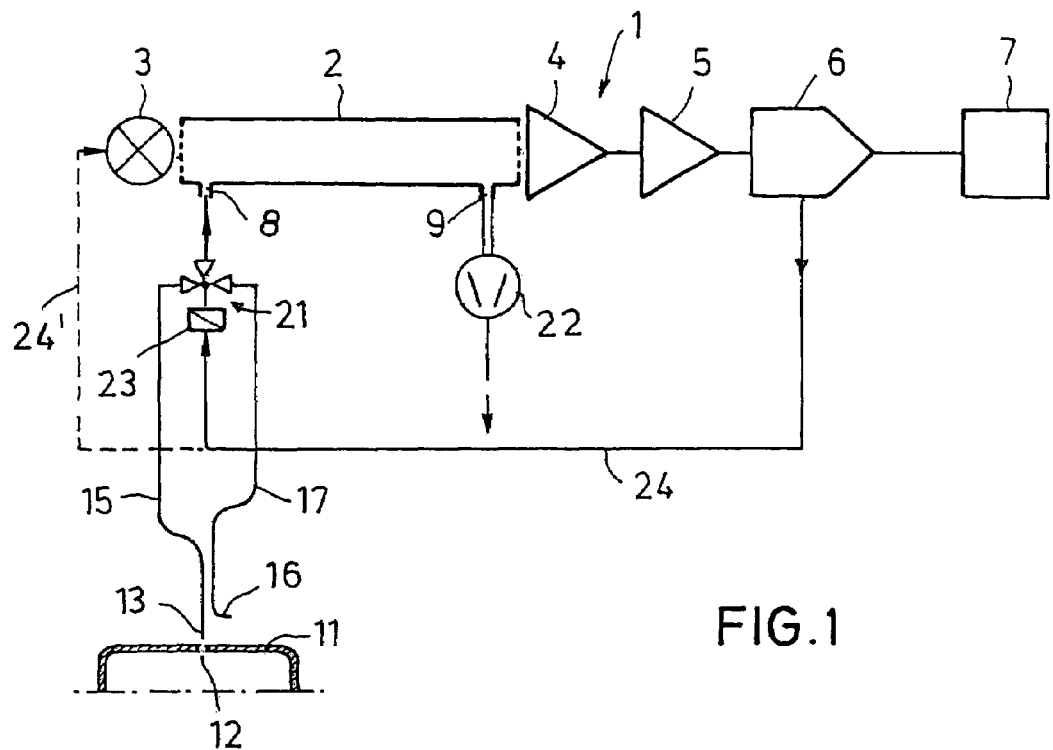

METHOD FOR DETECTING A GAS USING AN INFRARED GAS ANALYSER AND GAS ANALYSER SUITABLE FOR CARRYING OUT SAID METHOD

The present invention relates to a method for detecting a test gas that may be present at a measuring location, said test against having the characteristics of patent claims 1 and 2, as well as an infrared gas analyser suited for performing these methods.

Processes and devices of this kind are known from DE-A-199 11 260. These are in particular suited for applications in the area of sniffer leak detection. In sniffer leak detection, an object under test containing a working gas is scanned by means of a sniffer tip into which the measurement gases are drawn. If a leak is present, the working gas will escape to the outside. This is then supplied via the sniffer tip to the gas detector. If the working gas is not active within the infrared range, then a test gas which is active in the infrared range is added to the working gas in the object under test. In this instance, the measurement gas penetrating a possibly present leak consists of a mixture of working gas and test gas. If the working gas is already itself active in the infrared range (a halogen gas, for example), then itself may act as the test gas (or measurement gas).

In the area of sniffer leak detection there exists the problem that the sniffer tip will not only suck in test gases escaping from a possibly present leak (measurement location), but also gases from the vicinity of the measurement location. If these already contain low concentrations of the test gas, for example from previously determined leaks or from filling stations of a production line, these will also be recorded by the gas detector. At high test gas backgrounds this can cause erroneous measurements, i.e. that leak-tight objects under test are "detected" as being faulty.

In order to avoid disadvantages of this kind, it is proposed in DE-A-199 11 260 that the test gas concentration of the gas taken up at the measurement location be compared with the test gas concentration of the reference gas (gas taken up in the vicinity of the measurement location) with the aid of two cuvettes, a measurement cuvette and a reference cuvette, so as to take into account interfering influences. The use of two separate cuvettes with one or two precisely modulated infrared light sources is not only involved engineering-wise, but has also some disadvantages. One of these disadvantages is that the cuvettes do not change their properties in a uniform manner. They can collect contaminants in a non-uniform manner; when employing two infrared light sources these may age differently. In the document mentioned as being state-of-the-art it is proposed that it is also possible to employ only one infrared light source. However, this necessitates splitting of the beam. Such beam splitting and also merging of the beams detailed also in said document (for the purpose of employing only one infrared detector) results in relatively high losses (50% approx.) through which in particular the sensitivity of the gas analyser is impaired.

It is the task of the present invention to simplify methods and devices of the kind affected here, in particular with respect to improving their sensitivity.

This task is solved through the present invention by the characteristics of the patent claims.

In the methods and devices according to the present invention only one cuvette is required. Contamination and changes to the entire beam path (lamp-cuvette-detector) have an equal effect during both the measurement gas cycle and during the reference gas cycle. The single infrared light source must not necessarily be modulated, the modulation is attained by exchanging the gas. Above all, the esspecially precise modulation required for the state-of-the-art can be omitted, i.e. slower and brighter light sources may be employed, this being especially beneficial to the sensitivity of the analyser. Also beam splitting and beam merging are omitted. The single cuvette is at times filled with the measurement gas possibly containing the test gas, and at times with the reference gas (or additionally with the reference gas). If the concentration of the test gas in the measurement gas, i.e. at the measurement location, is greater than the concentration of the test gas in the reference gas, the infrared detector will detect an alternating signal which is a measure for the difference in concentration. In this, it does not matter whether or not a test gas background is actually present. Finally, from this there results the advantage that in the instance of the present invention the zero line (measurement gas=reference gas) is considerably more stable compared to the state-of-the-art, because in the instance where measurement gas and reference gas are identical during the gas exchange, no modulation component is generated. In contrast to this, in the instance of the state-of-the-art, two relatively large modulated signals needed to compared with each other which generally involves interfering components of significant magnitude.

Within the scope of the present invention it is beneficial to provide means for monitoring the operation of the infrared gas analyser according to the present invention, so as to avoid erroneous measurements caused by contamination or faults. Contaminants may not only impair the gas supply; also the sensitivity of the gas analyser itself decreases with increasing contamination.

For the purpose of avoiding an impaired gas supply, it is proposed to utilise the pressure in the gas supply lines as the measurement quantity for monitoring the flow. Monitoring the operation of the gas analyser itself is performed in accordance with the present invention such, that the infrared light source is modulated with a reference frequency, the signal of which is continuously monitored at the infrared detector (preferably with its own lock-in processing).

Finally, it is particularly expedient to employ a gas lamp as the infrared light source said gas lamp containing—at least a share—of the test gas. Compared to incandescent lamps, gas lamps offer the general benefit of being brighter (improved utilisation of the luminous power) and that they can be switched—modulated—faster. Since an infrared detector has a limited signal to noise ratio, the resolution of the analyser will increase with the brightness of the light source.

As gas lamps, flashlights, gas discharge lamps, glow lamps or alike may be employed. Since these are operated with the gas which is to be detected, filters can be omitted. Moreover, a wide range of the absorption spectrum may be utilised since the generated spectrum and the spectrum of the measurement gas substantially agree. The share of the utilised luminous power is high, through which there results a significantly improved gas selectivity of the infrared detector. The conversion to a different type of gas can be performed simply in that a gas lamp with a different type of gas is employed.

Further advantages and details of the present invention shall be explained with reference to the embodiments depicted in drawing FIGS. 1 to 6.

Depicted in drawing FIGS. 1 to 4 are infrared gas analysers with different facilities for supplying the measurement gas and the reference gas to a single cuvette. This is performed in the embodiments according to drawing FIG. 1 with the aid of a valve system, according to drawing FIG. 2 via an intermediate volume with a linearly moving piston, according to drawing FIG. 3 via an intermediate volume with a rotary/oscillating piston and according to drawing FIG. 4 via a throttle (measurement gas) and a valve (reference gas).

Figure 5:
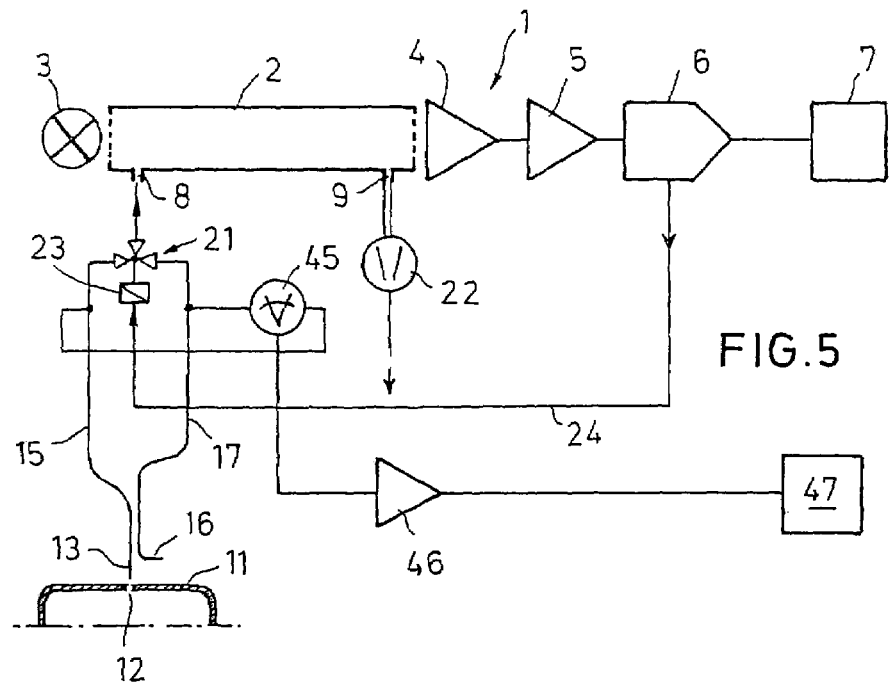

Drawing FIG. 5 depicts an embodiment for monitoring the flow through a sniffer.

Figure 6:
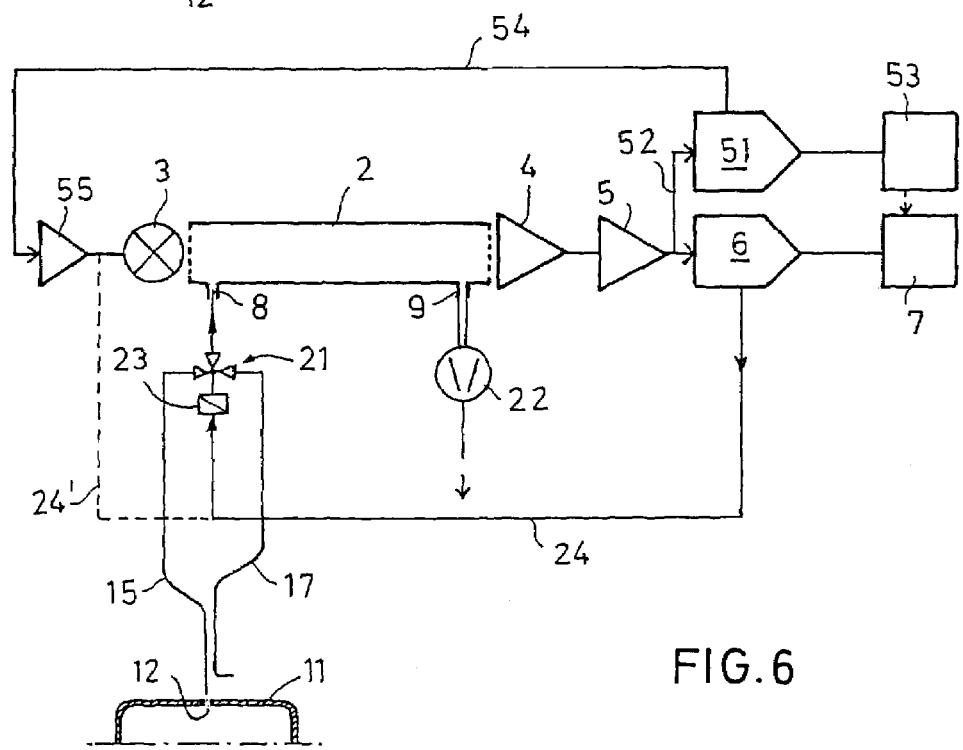

In drawing FIG. 6 an embodiment is presented which is equipped with means for checking its operation.

In all drawing figures the infrared gas analyser is generally designated as 1, its cuvette as 2, the infrared light source located on one face side as 3, the detector located on the opposite face side as 4, the connected electronic subassembly (amplifier/filter) as 5, a thereto connected further electronic subassembly (lock-in amplifier) serving the purpose of signal processing as 6, and a display as 7. Lock-in processing is commonly performed in software within a microcontroller; only for the purpose of being able to provide a better explanation, a separate block 6 is depicted. The cuvette 2 is equipped with connections 8 and 9 at its respective face sides. Via said connections the measurement gas and the reference gas is supplied, respectively discharged, in accordance with the methods described below.

The face sides of the cuvette 2 are represented by dashed lines in each instance. These shall indicate that the substantially gas-tight side walls of the cuvette are capable of passing infrared light in the area of the face sides. As infrared sources of light and infrared detector, facilities may be employed as detailed in DE-A-199 11 260.

In all examples of embodiments, sniffer leak detection has been selected as the application subject to the present invention. 11 designates an object under test which is to be analysed for the presence of leaks, said object having a leak 12. In this instance, the location of the leak is the measurement location. The sniffer tip 13 serves the purpose of taking up the measurement gas which, owing to the presence of leak 12, contains test gas. Via a line 15 connected to the sniffer, the taken in measurement gas flows to cuvette 2. Opening 16 in the hose line 17 serves the purpose of taking up gas from the vicinity of the sniffer tip (reference gas). This gas may contain a test gas background which during the determination of the concentration of the gas flowing out of the leak 12 shall be taken into account.

In the embodiment according to drawing FIG. 1 a control valve 21 serves the purpose of alternately supplying the measurement gas and the reference gas. It is so designed that either line 15 or the line 17 is connected to the inlet connection 8 of the cuvette 2. The gas in each instance flows through the cuvette in the axial direction and exits it through the discharge connection 9 which is linked to a supply or vacuum pump 22. This pump will define, depending on its pumping speed, the velocity of the flow of the gases to be analysed within the cuvette 2.

The gas exchange is preferably performed periodically. To this end, the control unit 23 of the control valve 21 is linked via the line 24 to the lock-in amplifier 6. The reliance on the basically known lock-in technology has the advantage that the wanted signal can be filtered in a frequency- and a phase-selective manner. Thus interfering signals are suppressed very effectively. In the instance where also the infrared light source 3 shall be modulated synchronously with the gas exchange, this light source is also linked to the lock-in amplifier 6. This variant is indicated by the dashed line 24[-1)]. Lock-in processing including control may also be performed by a microcontroller system with suitable software.

Figure 2:
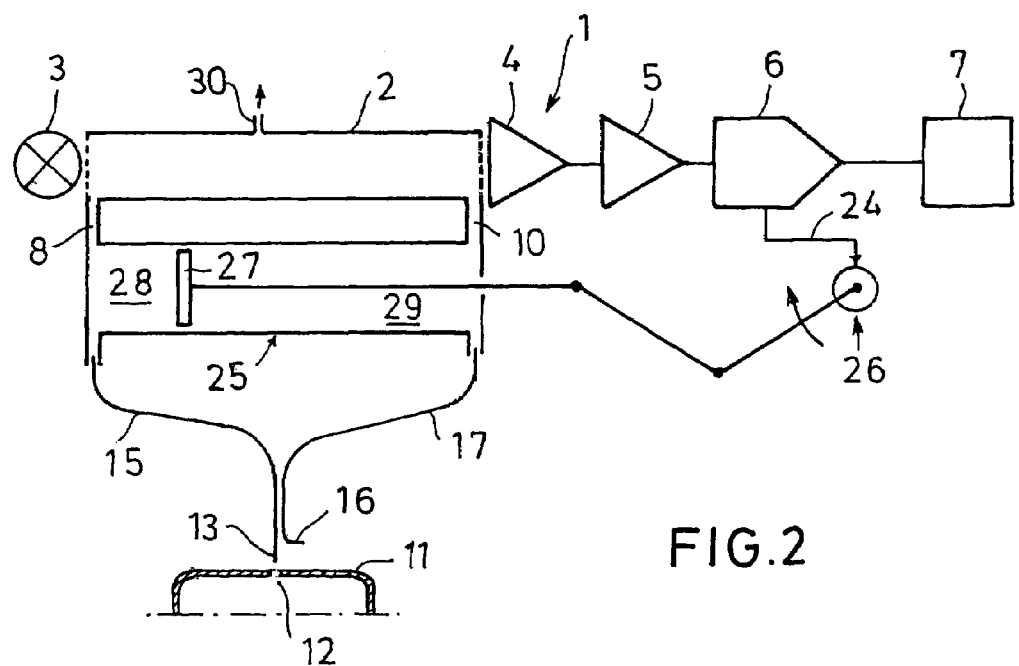

In the embodiment according to drawing FIG. 2 there is located between the cuvette 2 and the lines 15, 17 a preferably cylindrically designed intermediate volume 25—as depicted—in which there is located a piston 27 joined to a crank drive 26. The lines 15 and 17 each open out in the area of the opposing face sides of the intermediate volume 25. In these areas the intermediate volume is also linked to the inlet connections 8 and 10 at the cuvette 2. The piston 27 forms in the intermediate volume two separate chambers 28, 29. Chamber 28 serves the purpose of accepting and discharging the measurement gas, chamber 29 serves the purpose of accepting and discharging the reference gas. The to-and-fro motion of the piston 27[2)] effects an alternating supply of measurement gas and reference gas into the cuvette 2. The supplied gases exit the cuvette via the discharge connection 30 arranged expediently approximately at the middle of the cuvette 2, said connection being connected to the pump 22 (drawing FIG. 1). In comparison to the embodiment in accordance with drawing FIG. 1, the gas is exchanged in cuvette 2 more rapidly and more completely.

Figure 3:
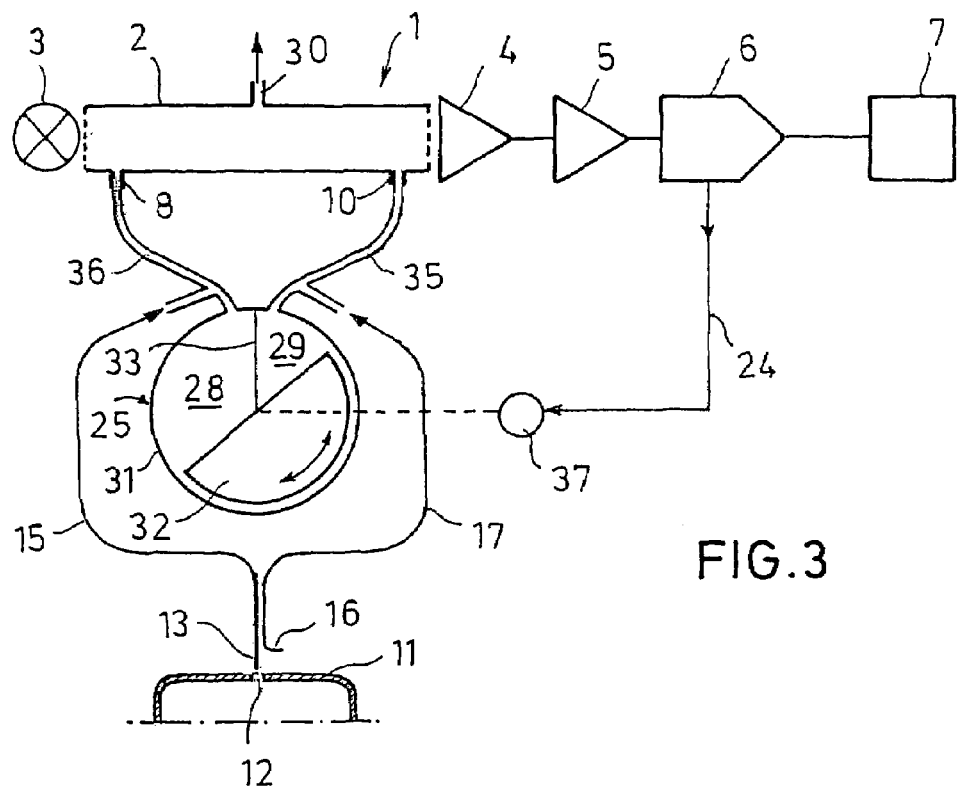
Figure 4:
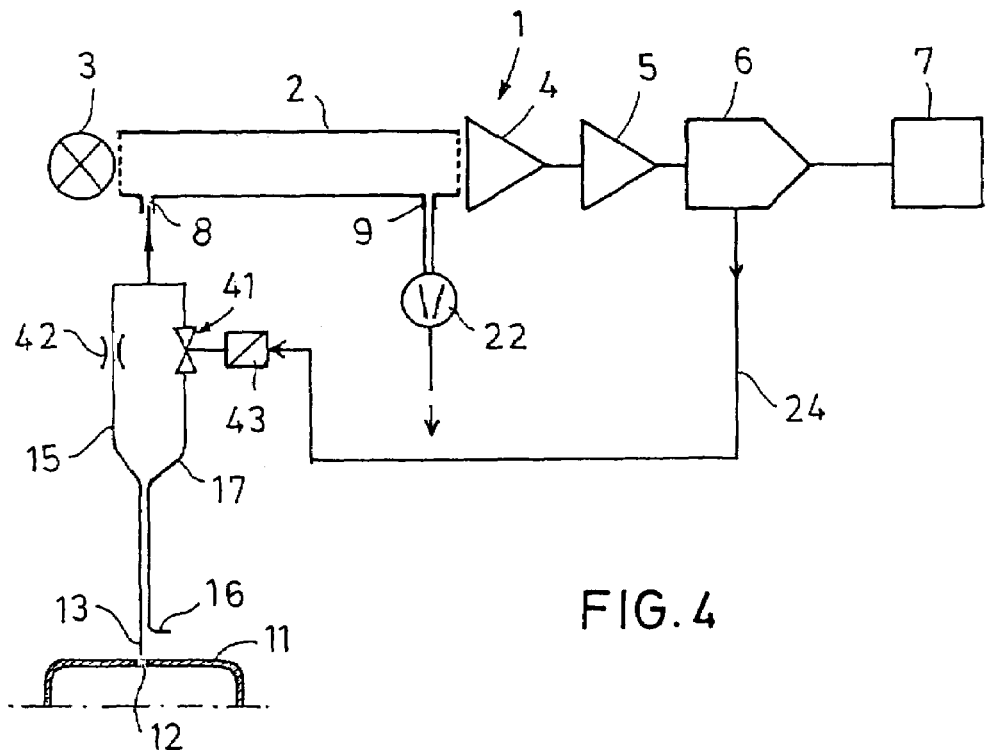

Also in the embodiment in accordance with drawing FIG. 3 there is present an intermediate volume 25 with the chambers 28, 29. These are formed by a housing 31 having a circular cross-section, a rotary/oscillating piston 32 having the cross-section of a semicircle, and a radial separating wall 33. The chambers 28, 29 are linked via the lines 35, 36 to the connections 8, 10[3)] of the cuvette 2. Lines 15, 17 open out into lines 35, 36 in such a manner, that an oscillating motion of the piston 32 produced by drive 37, alternately fills the cuvette 2 with measurement gas and with reference gas. These are gases exit the cuvette 2 via the middle connection 30.

The rate at which the periodic gas exchange in the cuvette 2 is effected in the instance of the embodiments in accordance with drawing FIGS. 1, 2 and 3 is defined by the lock-in amplifier 6. This amplifier is linked in each instance via the line 24 to the valve 21, the crank drive 26 or the drive at 37 of the oscillating piston 32. Rates of one second to ⅙ second per period have been found to be expedient.

In the embodiments in accordance with drawing figure is 1 to 3 the cuvette 2 is filled during a first period with the measurement gas and during second period with the reference gas. In contrast to this in the instance of the embodiment in accordance with drawing FIG. 4, the measurement gas is supplied continuously into the cuvette 2 via the line 15. The reference gas is only periodically supplied specifically via the valve 41 with its control unit 43, said valve being incorporated in line 17. The opening and closing times of this valve are also defined by the clock rate defined by the lock-in amplifier 6.

During measurement operations, the reference gas and the measurement gas, respectively reference gas only, also alternately flow through the cuvette 2. If the measurement gas contains test gas escaping from a leak, the detector 4 supplies the desired alternating signal.

Since leak rate sensitivity depends on the flow of the measurement gas respectively the flow of the test gas (high sensitivity at low measurement gas flow), it is expedient to equip line 15 with a throttle 42, so rated that the flow of the measurement gas will fill the cuvette with the measurement gas within half a period. In contrast to this, the flow of the reference gas may be high since practically enough reference gas is available.

Moreover, there exists in all embodiments the possibility of selecting a shorter measurement cycle for the reference gas compared to the measurement cycle for the measurement gas. Thus dead time is reduced, faster and/or more sensitive measurements are possible.

As already mentioned, the infrared light source needs not to be modulated with the clock of the lock-in amplifier since already the gas exchange effects the desired modulation. However, there exists the possibility of modulating the infrared light source 3 in addition synchronously to the gas exchange so as to attain sharper rising edges in the measurement signals. Without modulation, the edges of the measurement signal and depend on how rapidly the gas is exchanged.

Drawing FIG. 5 depicts, based on the embodiment in accordance with drawing FIG. 1, how the flow through sniffer at high sensitivity can be checked/monitored during operation. This is performed with the aid of a differential pressure sensor 45 which is linked at the level of the valve 21 to the lines 15, 17. The measured differential pressure signal is supplied via an amplifier 46 to processing logic 47. When analysing this differential pressure signal in a phase selective manner with respect to the switching frequency, one obtains information whether the flow in one or the other sniffer line or in both sniffer lines has changed. Also blockages in the line of the pump, respectively a fault in the pump are detected.

A different possibility of monitoring the differential pressure can be implemented with the aid of flow sensors. However, this is more involved compared to the method detailed above.

Drawing FIG. 6 also depicts, based on the embodiment in accordance with drawing FIG. 1, how the operation of the gas analyser 1 operating at high sensitivity can be checked/monitored. This may be applied in a solution in which the signal at the sensor is modulated with a fundamental frequency fg (supplied by the lock-in amplifier 6) and where the frequency-selective receiving unit determines the leak rate.

In the solution in accordance with drawing FIG. 6 there is provided a second lock-in amplifier 51 supplying a reference clock signal at a frequency fr. The inputs of the lock-in amplifiers 6 and 51 are connected to each other via line 52. At the output of the lock-in amplifier 51 there is connected a processing unit 53 which passes on its information to the display 7. Via the line 54 with the amplifier 55 the lock-in amplifier 51 is linked to the infrared light source 3.

In the embodiments depicted in drawing FIG. 6, the gas analyser 1 is monitored such that the infrared lamp 3 is modulated with an (additional) signal of a different frequency. In order to avoid interferences with the wanted signal fg, the selection of a frequency of, for example, fr=2.5 fg is expedient. The magnitude of the modulation must be selected such that this signal can be analysed well in a frequency-selective manner in the receiving unit. One then obtains a measurement signal with the frequency fg and a reference signal with the frequency fr which may be evaluated independently of each other. If, owing to a fault, system sensitivity should be reduced, this is detected by the decreasing amplitude of the signal component at fr (also when no leak is measured). Based on this it is possible to define the limits for an error message.

Processing is performed in block 53. Such processing can also serve the purpose of adapting the calibration factor at decreasing sensitivity, thereby increasing measurement accuracy.

In the drawing figures and descriptions separate blocks are depicted in each instance said blocks being components of the circuits employed. Expedient is the usage of integrated systems. For example, for lock-in processing, control and processing of the measurement and control signals, a microcomputer or a microprocessor circuit with attendant software may be employed.

The invention claimed is:

1. A method for detecting a test gas that may be present at a measuring location, using an infrared gas analyser said analyser comprising: a cuvette accepting the gases to be analysed; an infrared light source located at one face side of the cuvette; an infrared detector located at an opposite side of the cuvette, the signals from the infrared detector serving the purpose of determining test gas recorded at the measuring location; and two gas lines serving the purpose of supplying gases to the infrared gas analyser wherein a first of said gas lines is adapted to take up a measuring gas at said measuring location that may contain test gas and where a second gas line is adapted to take up gas from the surroundings of the measuring location (reference gas), which gas may contain a test gas background that is to be taken into consideration when detecting the test gas taken up at the measuring location, wherein only one cuvette is present, said method including the steps of:

taking up the measuring gas at the measuring location;

feeding the reference gas to the cuvette of the infrared gas analyser such that the reference gas and measuring gas are alternately present, and where only in the instance that at the measuring location test gas is taken up the concentration of which in the measuring gas is higher than the test gas concentration in the reference gas, do the alternating signals that are supplied by the infrared detector serve the purpose of determining the increased test gas concentration.

2. A method according to claim 1, including the step of employing a control valve that alternately connects the first gas line and the second gas line to a connection at the cuvette.

3. A method according to claim 1, including the step of employing an intermediate volume with a piston located between the cuvette and the first and second gas lines for alternately supplying reference gas and measuring gas to said cuvette.

4. A method according to claim 1, wherein for signal processing lock-in technology is employed.

5. A method according to claim 1, including the step of arranging the measurement cycle of the measuring gas to be longer than the measurement cycle of the reference gas.

6. A method according to claim 1, including the step of constantly monitoring the operation of the gas analyzer.

7. A method according to claim 6, including the additional steps of exchanging the measuring gas and the reference gas in the cuvette at a fundamental frequency fg; and modulating the infrared light source with a reference frequency fr.

8. A method according to claim 6, wherein the constant monitoring of the analyzer step includes the step of modulating the infrared light source synchronously to the gas exchange.

9. A method according to claim 1, including the step of constantly monitoring the gas flow.

10. A method according to claim 9, wherein the constant gas flow monitoring step includes the step of measuring the pressures in each of the first and second gas lines, wherein the difference between said pressures serves as a measurement quantity for monitoring the gas flow.

11. A method for detecting a test gas that may be present at a measuring location, using an infrared gas analyser, said analyser comprising: a cuvette accepting the gases to be analysed, an infrared light source located at one face side of the cuvette, an infrared detector located at the other face side of the cuvette, the signals from the infrared detector serving the purpose of determining test gas recorded at the measuring location, and two gas lines serving the purpose of supplying gases to the infrared gas analyser in which a first of said gas lines is adapted to take up a measuring gas at said measuring location that may contain test gas and a second of said gas lines is adapted to take up gas from the surroundings of the measuring location (reference gas), which gas may contain a test gas background that is to be taken into consideration when detecting the test gas taken up at the measuring location, wherein only one cuvette is present, said method including the steps of:

taking up the measuring gas at the measuring location: and feeding the reference gas to the cuvette of the infrared gas analyser such that the measuring gas taken up at the measuring location constantly flows through the cuvette; and adding reference gas to the cuvette periodically and where only in the instance that at the measuring location test gas is taken up, the concentration of which is higher than the test gas concentration in the reference gas, do the alternating signals supplied by the infrared detector serve the purpose of determining the increased test gas concentration.

12. A method according to claim 11, wherein for signal processing lock-in technology is employed.

13. A method according to claim 11, including the step of arranging the measurement cycle of the measuring gas to be longer than the measurement cycle of the reference gas.

14. A method according to claim 11, including the step of constantly monitoring the operation of the gas analyzer.

15. A method according to claim 14, wherein the constant monitoring of the analyzer includes the steps of exchanging gas at a fundamental frequency fg; and modulating the infrared light source with a reference frequency fr.

16. A method according to claim 14, wherein the constant monitoring of the analyzer step includes the step of modulating the infrared light source synchronously to the gas exchange.

17. A method according to claim 11, including the step of constantly monitoring the gas flow.

18. A method according to claim 17, wherein the constant gas flow monitoring step includes the step of measuring the pressures in each of the first and second gas lines, wherein the difference between said pressures serves as a measurement quantity for monitoring the gas flow.

19. An infrared gas analyzer for detecting a test gas that may be present at a measuring location said analyzer comprising:

a cuvette accepting the gases to be analyzed;

an infrared light source located at one face side of the cuvette;

an infrared detector located at an opposite side of the cuvette, the signals from the infrared detector serving the purpose of determining test gas recorded at the measurement location; and first and second gas lines serving the purpose of supplying gases to the infrared gas analyser wherein the first gas line is adapted to take up a measuring gas at a measuring location that may contain test gas and where the second gas line is adapted to take up gas from the surroundings of the measuring location (reference gas), which gas may contain a test gas background that is to be taken into consideration when detecting the test gas taken up at the measuring location, wherein only one cuvette is present wherein said device further includes means for admitting measuring gas taken up at the measuring location and the reference gas into the cuvette of an infrared gas analyser in such a manner that they are alternately present in the cuvette and in which said analyzer provides alternating signals indicative of an increased test gas concentration at the measuring location only when the measuring location test gas concentration is higher than the test gas concentration of said reference gas.

20. An analyzer according to claim 19, wherein the gas admitting means includes a control valve, which alternately connects the first gas line containing the measuring gas and the second gas line containing the reference gas to the cuvette.

21. An analyzer according to claim 19, wherein the gas admitting means includes an intermediate volume having two separate chambers through which with the aid of a piston, measuring gas and reference gas is alternately supplied to the cuvette.

22. An analyzer according to claim 19, wherein the cuvette is equipped with a discharge connection to which a supply/vacuum pump is connected.

23. An infrared gas analyzer for detecting a test gas that may be present at a measuring location, said analyzer comprising:

a cuvette accepting the gases to be analysed;

an infrared light source located at one face side of the cuvette;

an infrared detector located at the other face side of the cuvette, the signals from the infrared detector serving the purpose of determining test gas recorded at the measuring location; and two gas lines serving the purpose of supplying gases to the infrared gas analyser in which a first of said gas lines is adapted to take up a measuring gas at a measuring location that may contain test gas and a second of said gas lines is adapted to take up gas from the surroundings of the measuring location (reference gas), which gas may contain a test gas background that is to be taken into consideration when detecting the test gas taken up at the measuring location, wherein only one cuvette is present, wherein the measuring gas is taken up at the measuring location and the reference gas is fed to the cuvette such that the measurement gas taken up at the measuring location constantly flows through the cuvette, and gas admitting means for adding reference gas at times wherein said analyzer provides alternating signals indicative of an increased test gas concentration only when the measuring location test gas concentration is higher than the test gas concentration of the reference gas, said gas admitting means including a control valve in the second gas line serving the purpose of supplying the reference gas.

24. An analyzer according to claim 23 including a throttle in the first gas line for supplying the measuring gas.

25. An infrared gas analyzer for detecting a test gas that may be present at a measuring location, said analyzer comprising:

a cuvette accepting the gases to be analyzed;

an infrared light source located at one face side of the cuvette;

an infrared detector located at an opposite side of the cuvette, the signals from the infrared detector serving the purpose of determining test gas recorded at the measuring location;

two gas lines serving the purpose of supplying gases to the infrared gas analyser wherein a first of said gas lines is adapted to take up a measuring gas at a measuring location that may contain test gas and where a second gas line is adapted to take up gas from the surroundings of the measuring location (reference gas), which gas may contain a test gas background that is to be taken into consideration when detecting the test gas taken up at the measuring location, wherein only one cuvette is present; and gas admitting means for admitting measuring gas taken up at the measuring location and the reference gas into the cuvette such that the reference gas and measuring gas are alternately present, and only in the instance that at the measuring location test gas is taken up, the concentration of which in the measuring gas is higher than the test gas concentration in the reference gas, do the alternating signals supplied by the infrared detector serve the purpose of determining the increased test gas concentration, wherein for signal processing lock-in technology is employed including at least one lock-in amplifier as a component of the electronics, and a line carrying a clock signal from said amplifier being connected to at least one of said gas admitting means and said infrared light source.

26. An analyzer according to claim 25, including at least one of a microcomputer and a microcomputer circuit for the purpose of lock-in processing, control and processing of the measurement and control signals using attendant software.

27. An infrared analyzer for detecting a test gas that may be present at a measuring location, said analyzer comprising:

a cuvette accepting the gases to be analyzed;
an infrared light source located at one face side of the cuvette;
an infrared detector located at an opposite side of the cuvette, the signals from the infrared detector serving the purpose of determining test gas recorded at the measuring location;

two gas lines serving the purpose of supplying gases to the infrared gas analyser wherein a first of said gas lines is adapted to take up a measuring gas at a measuring location that may contain test gas and where a second gas line is adapted to take up gas from the surroundings of the measuring location (reference gas), which gas may contain a test gas background that is to be taken into consideration when detecting the test gas taken up at the measuring location, wherein only one cuvette is present, and in which measuring gas is taken up at the measuring location and reference gas is fed to the cuvette such that the reference gas and measuring gas are alternately present;

gas admitting means for admitting measuring gas taken up at the measuring location and the reference gas into the cuvette such that the reference gas and measuring gas are alternately present, and only in the instance that at the measuring location test gas is taken up, the concentration of which in the measuring gas is higher than the test gas concentration in the reference gas, do the alternating signals supplied by the infrared detector serve the purpose of determining the increased test gas concentration; and means for constantly monitoring the operation of the gas analyzer including means for exchanging the measuring gas and the reference gas at a fundamental frequency fg and means for modulating the infrared light source with a reference frequency fr including a second lock-in amplifier, the line carrying the clock signal for the reference frequency being connected to the infrared light source.

28. An analyzer according to claim 27, wherein the reference frequency fr is greater, by a factor of approximately 2.5 as compared to the fundamental frequency fg.

29. An analyzer according to claim 27, wherein the second lock-in amplifier is linked to a processing unit for detecting a system fault.

30. An analyzer according to claim 29, wherein the processing unit is also employed for adapting a calibration factor.

31. An infrared gas analyzer for detecting a test gas that may be present at a measuring location, said analyzer comprising:

a cuvette accepting the gases to be analyzed;
an infrared light source located at one face side of the cuvette;
an infrared detector located at an opposite side of the cuvette, the signals from the infrared detector serving the purpose of determining test gas recorded at a measuring location;

two gas lines serving the purpose of supplying gases to the infrared gas analyser wherein a first of said gas lines is adapted to take up a measuring gas at the measuring location that may contain test gas and where a second gas line is adapted to take up gas from the surroundings of the measuring location (reference gas), which gas may contain a test gas background that is to be taken into consideration when detecting the test gas taken up at the measuring location, wherein only one cuvette is present; and gas admitting means for admitting measuring gas taken up at the measuring location and the reference gas into the cuvette such that the reference gas and measuring gas are alternately present, and only in the instance that at the measuring location test gas is taken up the concentration of which in the measuring gas is higher than the test gas concentration in the reference gas, do the alternating signals supplied by the infrared detector serve the purpose of determining the increased test gas concentration, wherein said gas flow is being continuously monitored by said device including a differential pressure sensor connected to each of the first and second gas lines wherein the output of the pressure sensor is connected to processing logic.

32. An analyzer according to claim 31, wherein the processing logic contains its own lock-in amplifier.

33. An infrared gas analyser comprising:

a cuvette accepting gases to be analysed;
an infrared light source located at one face side of the cuvette;
an infrared detector located at the other face side of the cuvette, the signals from the infrared detector serving the purpose of determining test gas recorded at a measuring location;

two gas lines serving the purpose of supplying gases to the infrared gas analyser in which a first of said gas lines is adapted to take up a measuring gas at a measuring location that may contain test gas and a second of said gas lines is adapted to take up gas from the surroundings of the measuring location (reference gas), which gas may contain a test gas background that is to be taken into consideration when detecting the test gas taken up at the measuring location, wherein only one cuvette is present;

means for taking up the measuring gas at the measuring location;

means for admitting the reference gas to the cuvette such that the measuring gas taken up at the measuring location constantly flows through the cuvette wherein reference gas is added at times and only in the instance that at the measurement location test gas is taken up, the concentration of which is higher than the test gas concentration in the reference gas, do the alternating signals supplied by the infrared detector serve the purpose of determining the increased test gas concentration wherein for signal processing, a first lock-in amplifier processes the alternating signals to the detector; said analyzer further including a line carrying a clock signal from said first lock-in amplifier connecting at least one of the gas admitting means to said cuvette and to said infrared light source.

34. An analyzer according to claim 33, including at least one of a microcomputer and a microcomputer circuit for the purpose of lock-in processing, control and processing of the measurement and control signals using attendant software.

35. An infrared gas analyzer for detecting a test gas that may be present at a measuring location, said analyzer comprising:

a cuvette accepting gases to be analyzed;

an infrared light source located at one face side of the cuvette;

an infrared detector located at the other face side of the cuvette, the signals from the infrared detector serving the purpose of determining test gas recorded at measuring location;

two gas lines serving the purpose of supplying gases to the infrared gas analyser in which a first of said gas lines is adapted to take up a measuring gas at the measuring location that may contain test gas and a second of said gas lines is adapted to take up gas from the surroundings of the measuring location (reference gas), which gas may contain a test gas background that is to be taken into consideration when detecting the test gas taken up at the measuring location, wherein only one cuvette is present;

means for taking up the measuring gas at the measuring location; and means for admitting the reference gas to the cuvette such that the measuring gas taken up at the measuring location constantly flows through the cuvette wherein reference gas is added at times and only in the instance that at the measurement location test gas is taken up, the concentration of which is higher than the test gas concentration in the reference gas, do the alternating signals supplied by the infrared detector serve the purpose of determining the increased test gas concentration; and means for constantly monitoring the operation of the gas analyzer including means for exchanging gas at a fundamental frequency fg and modulating the infrared light source with a reference frequency fr, and further including a lock-in amplifier connected by a line to the infrared light source for carrying a clock signal for the reference frequency fr.

36. An analyzer according to claim 35, wherein the reference frequency fr is greater by a factor of approximately 2.5 as compared to the fundamental frequency fg.

37. An analyzer according to claim 35, wherein the lock-in amplifier is linked to a processing unit for detecting a system fault.

38. An analyzer according to claim 37, wherein the processing unit is further employed for adapting a calibration factor.

39. An infrared gas analyzer for detecting a test gas that may be present at a measuring location, said analyzer comprising:

a cuvette accepting the gases to be analyzed;

an infrared light source located at one face side of the cuvette;

an infrared detector located at an opposite side of the cuvette, the signals from the infrared detector serving the purpose of determining test gas recorded at a measuring location;

two gas lines serving the purpose of supplying gases to the infrared gas analyser wherein a first of said gas lines is adapted to take up a measuring gas at a measuring location that may contain test gas and where a second gas line is adapted to take up gas from the surroundings of the measuring location (reference gas), which gas may contain a test gas background that is to be taken into consideration when detecting the test gas taken up at the measuring location, wherein only one cuvette is present;

means for taking up the measuring gas at the measuring location;

means for admitting the reference gas to the cuvette such that the measuring gas taken up at the measuring location constantly flows through the cuvette wherein reference gas is added at times and only in the instance that at the measurement location test gas is taken up, the concentration of which is higher than the test gas concentration in the reference gas, do the alternating signals supplied by the infrared detector serve the purpose of determining the increased test gas concentration; and wherein said gas flow is being continuously monitored, said device including a differential pressure sensor connected to each of the first and second gas lines wherein the output of the differential pressure sensor is connected to processing logic.

40. An analyzer according to claim 39, wherein the processing logic contains its own lock-in amplifier.

* * * * *